(12) United States Patent
Barr (10) Patent No.: US 7,361,188 B2
(45) Date of Patent: Apr. 22, 2008

(54) PORTABLE CARDIAC MONITOR (75) Inventor: Keith E. Barr, Los Angeles, CA (US)

(73) Assignee: Exelys, LLC, Los Angeles, CA (US)

( * ) Notice: Subject to any disclaimer, the term of this patent is extended or adjusted under 35 U.S.C. 154(b) by 103 days.

(21) Appl. No.: 11/101,669

(22) Filed: Apr. 8, 2005

(65) Prior Publication Data
US 2006/0229521 A1 Oct. 12, 2006

(51) Int. Cl.
A61B 5/04 (2006.01)

(52) U.S. Cl. .................................... 607/509

(58) Field of Classification Search ................ 600/509, 600/523, 525; 607/27
See application file for complete search history.

(56) References Cited

U.S. PATENT DOCUMENTS

| 4,123,785 A | 10/1978 | Cherry et al. |
| 4,360,030 A * | 11/1982 | Citron et al. ............... 600/515 |
| 4,364,397 A * | 12/1982 | Citron et al. ............... 600/523 |
| 4,750,149 A | 6/1988 | Miller |
| 5,111,818 A | 5/1992 | Suzuki et al. |
| 5,228,450 A | 7/1993 | Sellers |
| 5,343,870 A | 9/1994 | Gallant et al. |
| 5,430,859 A | 7/1995 | Norman et al. |
| 5,701,894 A | 12/1997 | Cherry et al. |
| 5,876,351 A | 3/1999 | Rohde |
| 6,248,067 B1 | 6/2001 | Causey, III et al. |
| 6,317,625 B1 | 11/2001 | Olson et al. |
| 6,366,871 B1 * | 4/2002 | Geva ........................... 702/188 |
| 6,605,046 B1 * | 8/2003 | Del Mar ..................... 600/507 |
| 6,850,443 B2 | 2/2005 | Lofgren et al. |

OTHER PUBLICATIONS

U.S. Appl. No. 11/101,879, filed Apr. 8, 2005, Barr.
U.S. Appl. No. 11/101,880, filed Apr. 8, 2005, Barr.
U.S. Appl. No. 11/102,177, filed Apr. 8, 2005, Barr.
Leung et al. (1998). "Digitization of Electrocardiogram (ECG) Signals Using Delta-Sigma Modulation," Proceedings of the 20th Annual International Conference of the IEEE Engineering in Medicine and Biology Society, 20(4):1964-1966.
International Search Report and Written Opinion mailed May 15, 2007, for PCT Application No. PCT/US2006/45300 filed Nov. 21, 2006, 8 pages.

* cited by examiner

Primary Examiner—Carl Layno
Assistant Examiner—Brian T Gedeon
(74) Attorney, Agent, or Firm—Morrison & Foerster LLP (57) ABSTRACT A system and method for obtaining ECG signals from an ambulatory patient are disclosed herein. The system is configured to be inexpensive, small, and robust for outpatient monitoring. The system is configured to be a low power consuming device. The system provides options for a variety of settings and real-time access to the ECG signals being recorded during the recording period.

28 Claims, 7 Drawing Sheets

PORTABLE CARDIAC MONITOR

BACKGROUND OF THE INVENTION

The present invention relates to diagnostic medical devices. More particularly, the present invention relates to portable cardiac monitoring devices.

Through a combination of physiology, diet, and life-style factors, millions of people, just in the United States alone, have or will have some form of cardiovascular condition or disease. For many people, unfortunately, early symptoms of cardiovascular conditions are not obvious or even necessarily present. By the time the condition is apparent, it is often already at an advanced stage. At this point, therapeutic treatment options are limited, and such options are likely to carry considerable risks and costs. Early and accurate diagnosis is therefore critical to treat and stop further advance of cardiovascular conditions.

To this end, patients experiencing possible symptoms are encouraged to notify and be examined by health care professionals. Unfortunately, it may not be possible to accurately diagnose a possible condition if symptoms are generic or not present during examination. Alternatively, after a patient has been diagnosed and treatment decided, the patient's response to the treatment may need to be monitored so as to determine effectiveness and/or to fine-tune the treatment.

However, it is not practical for a health care professional to constantly monitor a patient for a set period of time, nor for a patient to stay at a clinic (or other locations with health care professionals) for a set period of time, merely for purposes of observing possible symptoms or responses. Instead, ambulatory patients are encouraged to be connected to a monitoring device for a set period of time while going about their regular routine.

An example of such a device is a Holter recorder that records cardiac signals of an ambulatory patient for a period of time, such as 24-72 hours. Holter recorders are typically configured to provide heart activity information, and in particular, electrocardiogram (ECG) recordings over a relatively long period of time. Such recordings permit identification of infrequent and transient disturbances of cardiac rhythm, which may aid in diagnosing patients with vague or intermittent symptoms such as dizziness, blackouts, or fainting spells. Such recordings may also quantify and pinpoint times and/or activities associated with a patient's infrequent symptoms. A physician may be interested not only in the unusual ECG events but also the background rhythm, which may comprise slower or overall responses to influences such as drug treatment, surgery, an implant, or stress. Moreover, a take-home diagnostic device provides more accurate and meaningful ECG recordings since the ambulatory patient is at a home setting (e.g., a natural or real setting) as opposed to an artificial setting (e.g. a doctor's office).

Effectiveness of ECG recording devices involve not only how well cardiovascular signals are measured and recorded, but also its ease of use and cost-effectiveness. Typical Holter recorders, unfortunately, are not inexpensive. Use of diagnostic devices, especially take home diagnostic devices, are also cost-effective and most beneficial for the end-customer (i.e., patients), but may in fact be more costly for medical practitioners due to device purchase and maintenance costs and loss of revenue from future appointments from a given patient. For clinics with budget constraints, spending thousands of dollars for each Holter recorder can be prohibitive.

Ease of use of typical Holter recorders is problematic. The electrode assemblies in typical ambulatory records are reused for many patients, sometimes up to several hundred patients per assembly. The electrode assemblies are not sterilized between uses. Patients can find the idea of having to wear such cables on their skin for up to several days to be unpleasant.

Typical Holter recorders also tend to be large and thus cumbersome for a patient to carry around at all times during the recording period. And even with the large size, typical Holter recorders can be inefficient in power consumption, which further requires use of large batteries.

Due to ease of use issues, it is not uncommon for patients to prematurely end the recording period. Alternatively, patients may be reluctant to even commit to the monitoring because of the degree of discomfort and interference with everyday activities.

Thus, there is a need for a small and lightweight monitoring and diagnostic device for obtaining ambulatory ECG signals. There is also a need for a device that can be taken home with an ambulatory patient for up to several days, provide sufficient data for therapeutic or diagnostic use by health care personnel, and is sufficiently robust and comfortable for take-home use. There is still a further need for a device that is inexpensive and is hygienic. Moreover, there is a need for a device that provides a variety of set-up and data optimization features while still being user-friendly.

BRIEF SUMMARY OF THE INVENTION

One embodiment of the invention relates to an ambulatory electrocardiogram (ECG) monitor. The monitor includes a recorder module, and a set of electrode leads coupled to the recorder module. The monitor further includes at least one cover that encases the recorder module. The ECG monitor is approximately 32 mm×52 mm×8 mm. The ECG monitor is attachable to patient's skin during a monitoring period.

Another embodiment of the invention relates to a method for obtaining electrocardiogram (ECG) waveforms from an ambulatory patient. The method includes coupling at least one disposable component to a recorder module, and attaching electrode leads and the recorder module to the ambulatory patient. The method further includes processing inputs from the electrode leads, and storing the processed inputs. The method still further includes powering a flash memory for a minimum duration of time necessary to transfer the stored inputs to the flash memory.

Still another embodiment of the invention relates to circuitry for obtaining electrocardiogram (ECG) signals associated with an ambulatory patient. The circuitry includes a first integrated circuit (IC) configured to accept differential channels of ECG signals, correct out-of-range ECG signals, and store processed ECG signals. The circuitry also includes a second IC in communication with the first IC, the second IC including a microcontroller. The circuitry also includes a third IC in communication with the second IC. The third IC is configured to store the processed ECG signals from the first IC. Each of the second and third ICs is selectively powered in response to an approximately full capacity of the stored processed ECG signals in the first IC. The average current consumption of the circuitry is less than 1 milliamp.

Yet still another embodiment of the invention relates to a portable cardiac recorder. The portable cardiac recorder includes means for delta-sigma modulating cardiac signals from a patient, and means for correcting the cardiac signals that are out-of-range within a data sampling period. The portable cardiac recorder further includes means for annotating certain of the cardiac signals in real-time, and means for radio frequency (RF) transmitting the cardiac signals. The portable cardiac recorder also includes means for storing the cardiac signals, and means for moisture proofing the recorder.

Other features and aspects of the invention will become apparent from the following detailed description, taken in conjunction with the accompanying drawings which illustrate, by way of example, the features in accordance with embodiments of the invention. The summary is not intended to limit the scope of the invention, which is defined solely by the claims attached hereto.

BRIEF DESCRIPTION OF THE OF THE DRAWINGS

The exemplary embodiments will become more fully understood from the following detailed description, taken in conjunction with the accompanying drawings, wherein the reference numerals denote similar elements, in which.

In the drawings, to easily identify the discussion of any particular element or part, the most significant digit or digits in a reference number refer to the figure number in which that element is first introduced (e.g., element 609 is first introduced and discussed with respect to FIG. 6).

DETAILED DESCRIPTION OF THE PREFERRED EMBODIMENTS

Described in detail below is a system and method for monitoring cardiovascular activity for therapeutic or diagnostic purposes. A portable monitor device is configured to record electrocardiogram (ECG) signals for a set period of time. The portable monitor device is configured to be small, inexpensive, and lightweight. The portable monitor device is configured for at-home or outpatient monitoring of ambulatory patients. Low power consumption and a variety of set-up and recording features are provided via a customized integrated circuit (IC).

The following description provides specific details for a thorough understanding of, and enabling description for, embodiments of the invention. However, one skilled in the art will understand that the invention may be practiced without these details. In other instances, well-known structures and functions have not been shown or described in detail to avoid unnecessarily obscuring the description of the embodiments of the invention.

Figure 1:
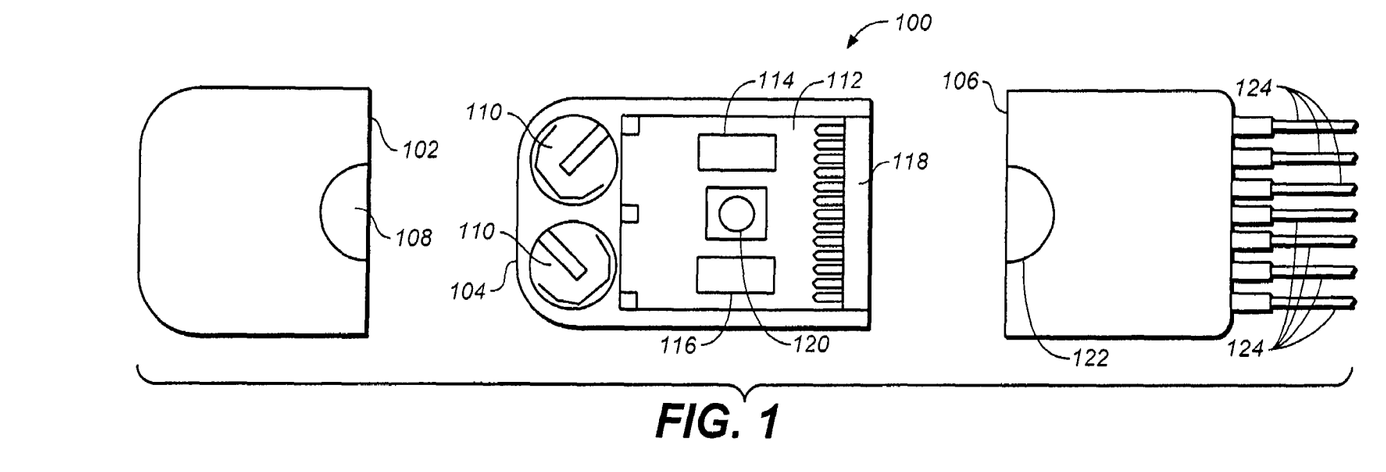
FIG. 1 is an exploded view of one embodiment of an electrocardiogram (ECG) monitor.

Referring to FIG. 1, an exploded view of one embodiment of a portable ECG monitor 100 is shown. The ECG monitor 100 includes a first cover 102, and a recorder module 104, and a second cover 106.

The first cover 102, also referred to as an end cover, is configured to slip over approximately half of the recorder module 104. The first cover 102 is hollow with an opening along one side. A cutout 108 is included at the opening edge of the first cover 102. The cutout 108 is shaped to fit around or encircle an annotate button 120 at the recorder module 104.

The recorder module 104 includes batteries 110, a printed circuit board (PCB) 112, a microcontroller integrated circuit (IC) chip 114, a converter IC chip 116, a pin connector 118, the annotate button 120, and a flash memory IC chip (not shown). The batteries 110 are provided at a first side of the recorder module 104. The batteries 110 are configured to power the ECG monitor 100. In one embodiment, the batteries 110 comprise two silver oxide button batteries, each battery having a diameter of approximately 12 millimeters (mm), a thickness of approximately 4 mm, and a voltage of 1.6 volts.

The PCB 112 is provided adjacent to the batteries 110. The microcontroller IC chip 114, converter IC chip 116, and the flash memory IC chip 400 are electrically coupled to the PCB 112. Although not shown, the PCB 112 includes a variety of electrical components such as capacitors, resistors, electrical leads, data bus, etc. typical for function of the recorder module 104.

The annotate button 120 is provided approximately at the center of the recorder module 104. The annotate button 120 is configured to be accessible when the ECG monitor 100 is in an open or closed position. The annotate button 120 is electrically coupled to the converter IC chip 116. In one embodiment, the annotate button 120 is actuated by applying a downward pressure (e.g., pushing). Alternatively, the annotate button 120 can be a switch, a toggle switch, or a variety of other two position devices. The annotate button 120, to be discussed in detail below, is utilized by a health care professional during the initialization or calibration process and/or by the patient to flag certain portions of the ECG data being obtained.

The pin connector 118 is provided at a side of the recorder module 104 opposite the side of the batteries 110. The pin connector 118 is electrically coupled to the PCB 112. In one embodiment, the pin connector 118 is a 30-pin connector. In another embodiment, the pin connector 118 may comprise less or more than 30 pins (e.g., 28 pins, 32 pins, etc.). In still another embodiment, the pin connector 118 may comprise a connection device other than pins as long as it is capable of high-speed communication with a separate computing device (to be discussed below).

The second cover 106, also referred to as an end cover, is configured to slip over the recorder module 104 (the side including the pin connector 118). The second cover 106 is hollow with an opening along one side. The opening includes a cutout 122 that is configured to fit around or encircle the annotate button 120. The cutouts 108 and 122 are symmetrical to each other.

The side of the second cover 106 opposite the cutout 122 includes a set of openings and connection points for a set of electrode leads 124. The second cover 106 is configured to permit the electrode leads 124 to be in electrical contact with the PCB 112 when the second cover 106 is fully slipped over the recorder module 104. The electrode leads 124 are detachable from the ECG monitor 100.

In one embodiment, the electrode leads 124 comprise a set of seven electrode leads. Six leads serve as three differential channel inputs leads. The seventh lead serves as a common or grounding lead. The electrode leads 124 are approximately less than 12 inches in length. Although not shown, the other ends of the electrode leads 124 are configured to continually contact a patient's skin for the duration of the recording period. Various adhesives and electrical contact configurations with the skin are well-known in the art. There may be less or more than seven leads, depending on the cardiac signals desired.

The second cover 106 optionally also includes an opening at the same side as the electrode leads 124 for the pin connector 118. With this additional opening, the pin connector 118 can be accessed with the second cover 106 fully slipped over the recorder module 104. Alternatively, the ECG monitor 100 can be configured such that the pin connector 118 is only accessible when the second cover 106 has been removed.

In one embodiment, the recorder module 104 measures approximately 30 mm×52 mm×5 mm, and weighs less than approximately 16 grams. Each of the first and second covers 102, 106 is comprised of molded plastic, such as polypropylene or polyvinyl chloride. It is contemplated that the recorder module 104 may be smaller than discussed above. As the ability to further miniaturize ICs, provide additional circuitry on a single chip, or more efficient power sources become available, the recorder module 104, and by extension, the ECG monitor 160, can be made smaller and/or lighter.

Figure 2:
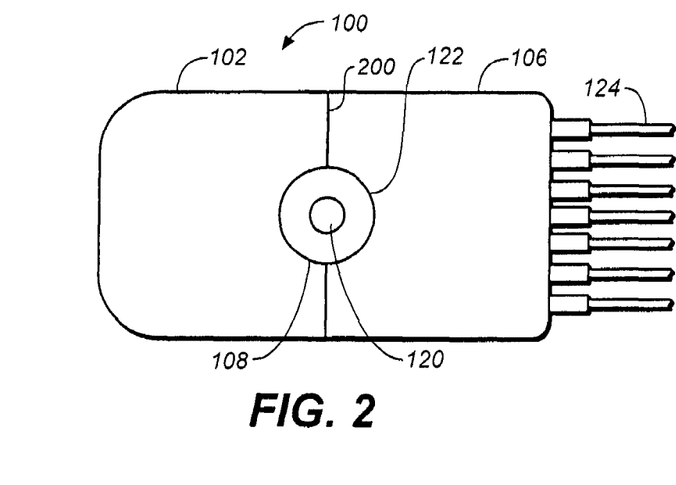
FIG. 2 is the ECG monitor of FIG. 1 in an assembled position.
Figure 3:
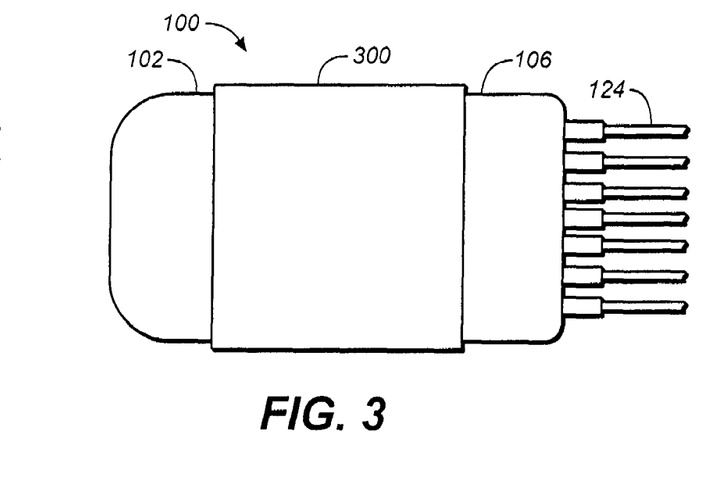
FIG. 3 is a back side of the ECG monitor of FIG. 1, shown with a moisture resistant sealant.

The ECG monitor 100 is shown in FIG. 1 in a disassembled or open position. The ECG monitor 100 assembled (in a closed position) is shown in FIGS. 2-3. In particular, FIGS. 1 and 2 illustrate a front view of the ECG monitor 100, and FIG. 3 illustrates a back view of the ECG connector 100. In FIG. 2, the first and second covers 102, 106 are fully slipped over the recorder module 104. The first and second covers 102, 106 contact each other at an equatorial seam 20. The respective edges of the first and second covers 102, 106 can form a frictional or snap fit with each other to form the equatorial seam 200.

The cutouts 108 and 122 are also configured such that in the assembled position, the cutouts 108 and 122 cincture the annotate button 120. In the assembled position, the electrode leads 124 are also in electrical contact with the PCB 112.

In FIG. 3, the back side of the assembled ECG monitor 100 is shown. After the first and second covers 102, 106 encapsulate the recorder module 104, a moisture resistant device 300 (also referred to as a moisture resistant sealer or sealant) is applied over the equatorial seam 200 and the annotate button 120. The moisture resistant device 300 has, for example, a width of approximately 36 mm. As an example, the moisture resistant device 300 comprises tape having at least one adhesive surface that wraps around the ECG monitor 100 and back onto itself. The tape comprises a waterproof or moisture resistant layer and a thick adhesive layer. In one embodiment, the thick adhesive layer provides adhesive properties and at least a certain amount of sealant properties (to aid in making the ECG monitor moisture resistant). The tape is also flexible enough to allow actuation of the annotate button 120. The moisture resistant device 300 can include polyvinyl chloride material, Mylar™ backing, or polyester backing.

With the moisture resistant device 300 wrapped around the ECG monitor 100, the ECG monitor 100 measures approximately 32 mm×52 mm×8 mm or less, and weighs approximately 28 grams or less.

Due to the inexpensiveness of each of the batteries 110, first cover 102, second cover 106, electrode leads 124, and moisture resistant device 300, one or more of these components can be disposable. A set-up kit comprising, for example, the moisture resistant device 300, batteries 110, and a set of the electrode leads 124 may be provided to the doctor, for one-time use with each patient. Utilizing such a kit for each patient addresses hygiene issues, and ensures best possible moisture-resistance and power source for each recording period. The recorder module 104 can be used repeatedly, as discussed in greater detail below.

The ECG monitor 100 includes at least four interfaces: the electrode leads 124, the pin connector 118, the annotate button 120, and a radio frequency (RF) interface. The electrode leads 124 are in electrical contact with an ambulatory patient's skin. The electrode leads 124 are distributed over the patient's chest region to obtain ECG signals in accordance with known ambulatory EKG standards, such as the EC38 standard.

The pin connector 118 permits two-way communication between the ECG monitor 100 and an another device. The another device may be a base station or a computing device. Among other things, initiation, calibration, feature selection (e.g., data sampling rate), and recorded data readout are possible via the pin connector 118. Such functions may be carried out without insertion of the batteries 110 in the ECG monitor 100. For example, the pin connector 118 may include a USB connector that mates with a USB connector included in the computing device (e.g., a laptop or general purpose computer), and obtain power to the monitor 100 from the computing device via the USB connection. Alternatively, the pin connector 118 may mate with a connector at the base station, and the base station electrically couples to the computing device via a cable.

The annotate button 120 is utilized by both the health care professional and patient. For the health care professional, the annotate button 120 is first held down, and then the batteries 110 are inserted while the annotate button 120 continues to be depressed. The annotate button 120 remains depressed after battery insertion for some minimum period of time (e.g., 5 seconds or 10 seconds). The recorder module 104 is thus cleared of data (e.g. clears or erases the flash RAM memory shown in FIG. 4) and is reset to start a new recording period. For the patient during his/her recording period, if there is a cardiac event that the patient wishes to flag to the physician who will later view the recorded ECG data signals, the patient can push down the annotate button 120 and a notation will be included with the ECG data signals at that point in time (e.g., real-time annotation of ECG signals). The patient may utilize this annotate feature at any time during the recording period and more than once during the recording period.

A recording period is the time starting immediately after initialization/calibration to when the monitor 100 stops recording for a given patient (because, for example, the batteries 110 can no longer supply sufficient power to the monitor 100, the batteries 110 are removed from the monitor 100, the flash memory IC chip 400 is full, or the electrode leads 124 are removed from the patient). A cardiac event, to be discussed in detail below, can be a variety of actual, perceived, or potential events associated with out-of-the-ordinary cardiac function. As examples, cardiac events can comprise symptoms such as irregular heartbeats, shortness of breath, dizziness, numbness to a section of the patient's body, irregular vision, increased perspiration, increased body temperature, chest pains, headaches, emotional distress, or psychological distress or stress. Cardiac events can also comprise external or environmental events that may attribute to out-of-the-ordinary cardiac function such as an argument, engaging in strenuous activity, receiving bad news, falling down, etc.

The RF interface is configured for short-range wireless data transmission between the ECG monitor 100 and the base station. The transmission range is less than approximately 12 inches. Real-time ECG data signals with the annotate information are transmitted to the base station. Correspondingly, the base station includes a RF receiver. In one embodiment, the base station is a small device about the size of a pack of cards. The base station is configured to be a conduit or interface between the ECG monitor 100 and a computer. In this manner, a general all-purpose computer can be utilized without the need for specialized circuitry or peripheral device(s). The RF data received by the base station can be provided to the computer via a cable. The RF data waveforms can then be displayed on the computer. The health care professional ensures that the batteries 100 are properly inserted and in working order via the RF interface. Proper adjustment of electrode leads 124 on the patient may also be performed from viewing the ECG waveforms.

It is contemplated that the ECG monitor 100 may have less than four interfaces. For example, the RF interface may be optional if no corresponding RF device (such as the base station) will be utilized. Alternatively, the ECG monitor 100 may include other interfaces to provide communication or functional features.

Figure 4:
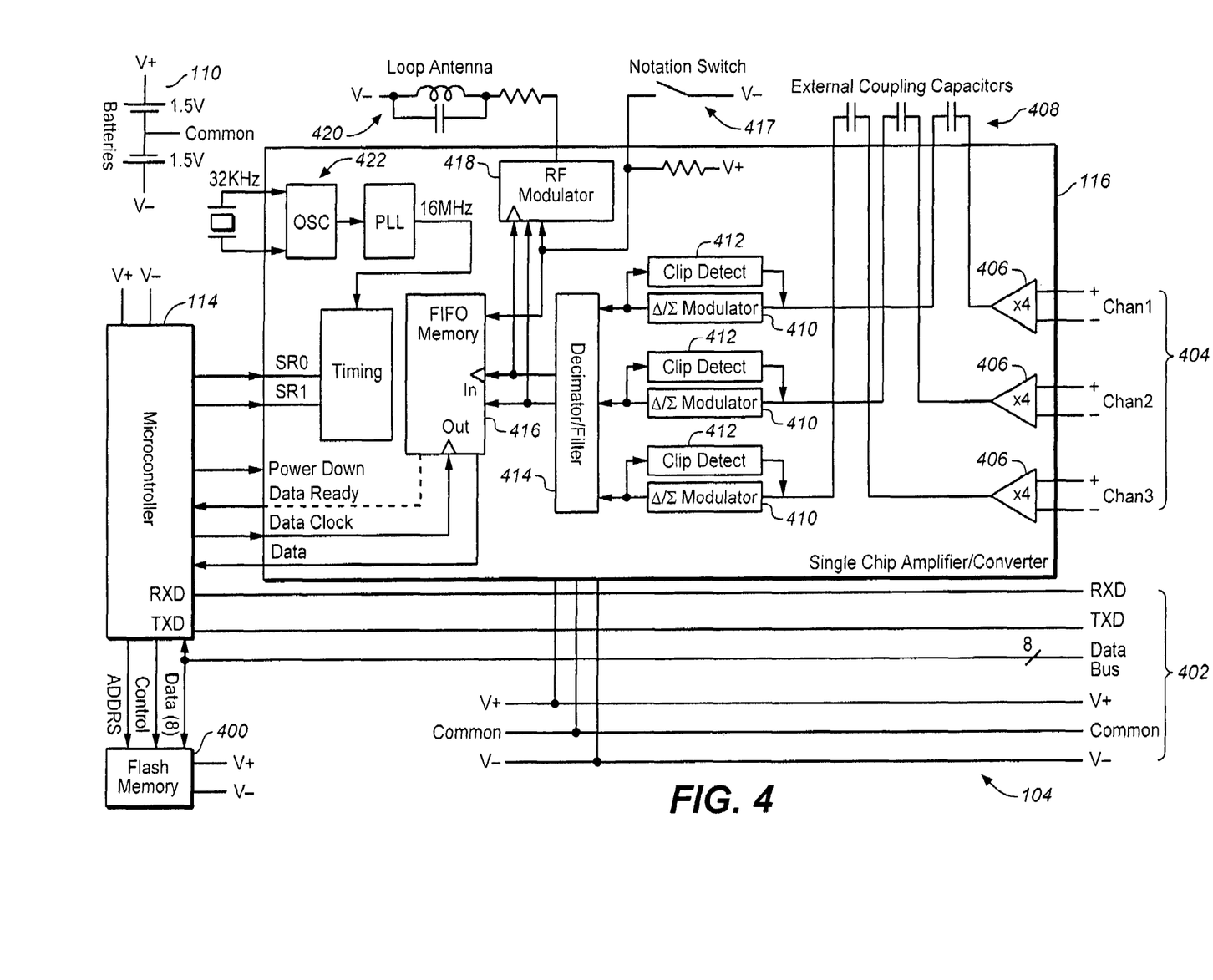
FIG. 4 is a block diagram of circuitry included in the ECG monitor of FIG. 1.

In FIG. 4, a block diagram of the circuitry included in the recorder module 104 is shown. The converter IC chip 116 is in communication with the microcontroller IC chip 114. The microcontroller IC chip 114 is in communication with a flash memory IC chip 400.

The electrode leads 124 provide the three pairs of differential channel inputs 404. Each pair of differential channel inputs 404 is representative of electrical potential (or physiological signals) sensed at a specified location on an ambulatory patient's chest region. Each pair of differential channel inputs 404 is associated with a set of differential amplifier 406, coupling capacitor 408, nth order delta-sigma modulator 410 (where n=1 to 5), and clip detector 412.

The differential channel inputs 404 are the inputs to three respective differential amplifiers 406. Each of the differential amplifiers 406 is configured to convert its respective pair of differential channel analog inputs 404 into a single-ended analog signal. Each of the differential amplifiers 406 provides a gain of approximately four (to handle up to a 300 mV input).

The outputs of the differential amplifiers 406 are the inputs to three respective coupling capacitors 408. A coupling capacitor 408 is provided between the differential amplifier 406 and the nth order delta-sigma modulator 410. As an example, the capacitance of each coupling capacitor 408 can range from approximately 0.1 μF to 3.3 μF, depending on the low frequency limit of the ECG monitor 100. The three coupling capacitors 408 are provided external to the converter IC chip 116, on the PCB 112.

Each of the clip detector 412 forms a feedback loop to the input of its respective nth order delta-sigma modulator 410. The outputs of the three nth order delta-sigma modulators 410 are inputs to a decimator 414. The decimator 414 is configured to operate in a time-share manner to process outputs of the three nth order delta-sigma modulators 410. Each nth order delta-sigma modulator 410 and the decimator 414 combination is also referred to as an analog-to-digital (A/D) modulator or converter.

For each pair of differential inputs 404, the coupling capacitor 408 and clip detector 412 are configured to detect ECG signals that are out of range to anticipate and correct subsequent ECG signals that are likely to be out of range. The clip detector 412 provides a corrective signal to adjust subsequent ECG signals to be within a diagnostically useful range. When the baseline or zero point of the ECG signals shifts outside of a prescribed signal range such that a positive or negative peak of the ECG signals are clipped, then such signals are considered to be out of range. If out of range signals are not corrected, and merely processed and stored the same way as in-range signals, then the stored out of range signals would store incomplete waveform information and not include the maximum and/or minimum signal inflections representative of actual cardiac electric potential (e.g., be diagnostically useful). Instead, the stored out of range signals would show, for example, a continuous maximum value (a clipped signal), and waveform information such as the actual signal maximum (relative to the rest of the signal), the changes in the signal amplitude, shape of the signal, etc. would not be captured. In contrast, diagnostically useful signals are signals that include ECG maximum and minimum inflection information, signal shape, etc. so that medically useful information is available to a health care professional that reviews the recorded ECG data (to make a diagnosis of a disease or illness, evaluate efficacy of a treatment, etc.).

As an example, an out of range signal could result from a patient's perspiration or when the patient undergoes physical stress due to an extreme cardiac event. The detection and "correction" occurs in less than a data sampling period. For example, when the output signal from the differential amplifier 406 is sixteen successive zeros or ones, then the signals are considered to be out of range. The subsequent analog signals (which have been corrected if out-of-range) are then digitized at the nth order delta-sigma modulator 410.

The digitized bit streams are inputted to the decimator 414. The decimator 414 is configured to output a high-resolution value for every 64 input bits (when the decimator 414 has a decimation ratio of 64:1). The output of the decimator 414 is a single bit stream that is the input to a first-in-first-out (FIFO) memory 416. Each of the nth order delta-sigma modulator 410 works in conjunction with the decimator 414 (also referred to as a decimation filter) to produce high accuracy samples. The nth order delta-sigma modulator 410 operates at high sample rates. The nth order delta-sigma modulator 410 generates a single bit output data stream that can be used to detect an upcoming saturation (or out of range) limit as well as being the input to the decimator 414.

The switch 417 is actuated by pushing down the annotate button 120. Information about the actuation (or non-actuation) of the switch 417 is associated with time corresponding ECG data in the FIFO memory 416.

The output of the decimator 414 and the switch 417 are also provided as inputs to a RF modulator 418. The RF modulator 418 configures the ECG and annotates signals suitable for RF transmission via a loop antenna 420. The loop antenna 420 and the switch 417 are located external to the converter IC chip 116. The loop antenna 420 provides real-time continuous output that is identical (in substantive content) to the data stored in the FIFO memory 416.

Also included in the converter IC chip 116 are clock components 422 to provide timing and synchronization functions associated with processing of the differential channel inputs and data transmission to other circuitry. The clock components 422 include a crystal oscillator operating at 32

KHz, a phase-lock loop (PLL) operating at 16 MHz, and a timing clock. The crystal oscillator is in communication with a (watch) crystal located external to the converter. IC chip 116. The crystal oscillator operating at a lower frequency and then achieving the desired frequency with a PLL provides total lower power consumption (e.g., on the order of 50 microamp) verses, for example, starting with a 16 MHz oscillator (which has power consumption of approximately 4 to 5 milliamp).

Figure 5:
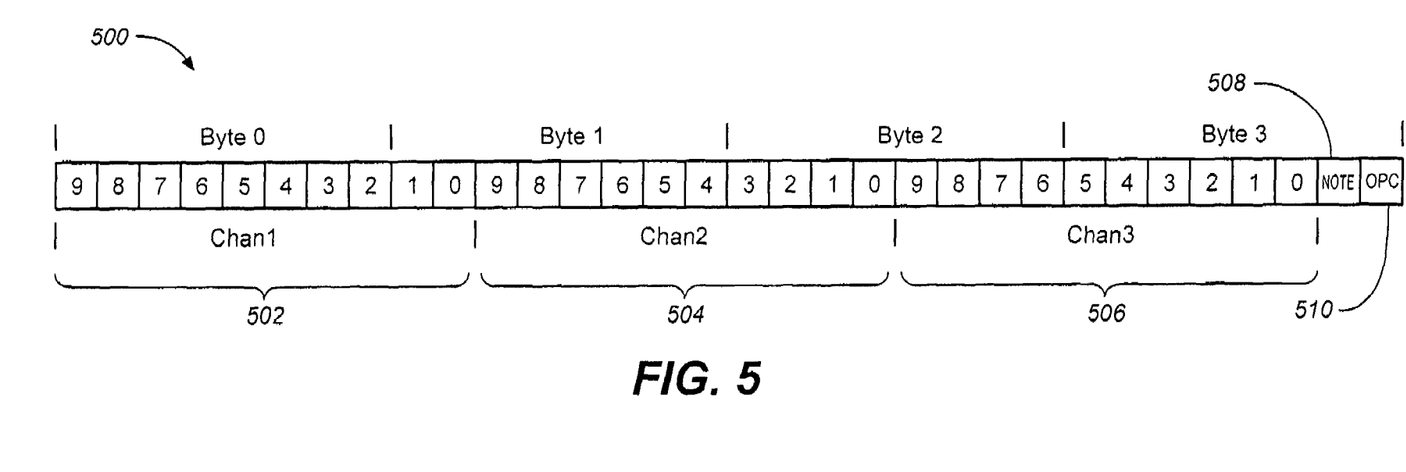
FIG. 5 is an illustration of a data format of data samples obtained by the ECG monitor of FIG. 1.

As shown in FIG. 5, the data format of each sample 500 stored in the FIFO memory 416 is 32 bits (4 bytes) in length. Of the 32 bits, there are 10 bits of information for each of the 3 channels (blocks 502, 504, 506), followed by a bit that indicates the condition of the switch 417 (block 508), and lastly a negative check bit (block 510; also referred to as a checksum). For example, the FIFO memory 416 has a capacity to store up to 16 samples with each sample being a 32 bit word.

Even though the ECG monitor 100 continuously monitors the electric potential information from the surface of the patient's skin throughout the recording period, the ECG monitor 100 operates on an average current of less than 10 milliamp or less than 1 milliamp. For example, the average current required can be around 700 microamp. Such low power consumption is possible due to the low power requirement of the converter IC chip 116 and selective or intermittent powering of the chips 114 and 400. This is in contrast to conventional ambulatory ECG recorders that consume on average around 50 milliamp of current.

When the FIFO memory 416 is full (or approaching full capacity), the microcontroller IC chip 114 is powered up. A DATA READY signal (see FIG. 4) is transmitted from the FIFO memory 416 to the microcontroller IC chip 114 to turn on or wake up the microcontroller IC chip 114. The microcontroller IC chip 114 is configured to transfer the data serially out of the FIFO memory 416 and then power down again when the data transfer is complete. A DATA CLOCK line and a DATA line are utilized by the microcontroller IC chip 114 to perform the data transfer.

The microcontroller IC chip 114 (also referred to as a microcomputer or microprocessor) is a programmable microprocessor that is configured to control transfer of data from the FIFO memory 416 to the flash memory IC chip 400, control access to the flash memory IC chip 400, and store certain settings relating to the ECG monitor 100. The flash memory IC chip 400 is a RAM memory device. During the recording period, both the microcontroller IC chip 114 and the flash memory IC chip 400 are only powered when the FIFO memory 416 needs to be emptied because the FIFO memory 416 is at or near maximum storage capacity. Once data transfer to the flash memory IC ship 400 is complete, both the microcontroller IC chip 114 and the flash memory IC chip 4000 are powered down to minimize power consumption.

The microcontroller IC chip 114 temporarily stores the data from the FIFO memory 416, calculates which portions of the flash memory IC chip 400 to write the data to, and writes such data to appropriate portions of the flash memory IC chip 400. The ADDRS, CONTROL, and DATA (8) lines between the microcontroller IC chip 114 and the flash memory IC chip 400 are utilized for the data transfer. The microcontroller IC chip 114 turns on the flash memory IC chip 400 when a write operation to the flash memory IC chip 400 is ready to commence (e.g., via the CONTROL line). Upon completion of the write operation, the microcontroller IC chip 114 turns off the flash memory IC chip 400, transmits a POWER DOWN signal to the converter IC chip 116 (to indicate that data transfer from the FIFO memory 416 to the flash memory IC chip 400 is complete), and then turns itself off.

Continuing the example of the FIFO memory 416 containing 16 samples of data and each sample being a 32 bit word, up to 512 bits of data would be transferred out of the FIFO memory 416 each time the DATA READY signal is transmitted. In the case of 128 Hz operation, 16 samples are acquired 8 times per second, thus the microcontroller IC chip 114 and flash memory IC chip 400 are turned on 8 times per second. In the case of 1024 Hz operation, the microcontroller IC chip 114 and flash memory IC chip 400 are turned on 64 times per second.

In one embodiment, the microcontroller IC chip 114 is awake for a time period on the order of approximately 500 µs per duty cycle. The power consumption of the microcontroller IC chip 114 during each awake period is on the order of approximately 20 milliamp, for example, 16 milliamp. The flash memory IC chip 400 is awake for a time period shorter than the awake period of the microcontroller IC chip 114 for each duty cycle. The awake period for the flash memory IC chip 400 is approximately 200 µs. The power consumption of the flash memory IC chip 400 during each awake period is on the order of approximately 30 milliamp, for example, 25 milliamp.

The microcontroller IC chip 114 is also configured to transmit the prescribed sample rate to the timing clock at the converter 116 via terminals SR0 and SR1.

Various leads 402 are associated with the pin connector 118. The leads 402 include receiver and transmitter lines to the microcontroller IC chip 114 (e.g., to specify the sample rate, or to prescribe the minimum length of time required for depression of the annotate switch 417 during initialization), and data bus lines to access the data stored in the flash memory IC chip 400.

Figure 6:
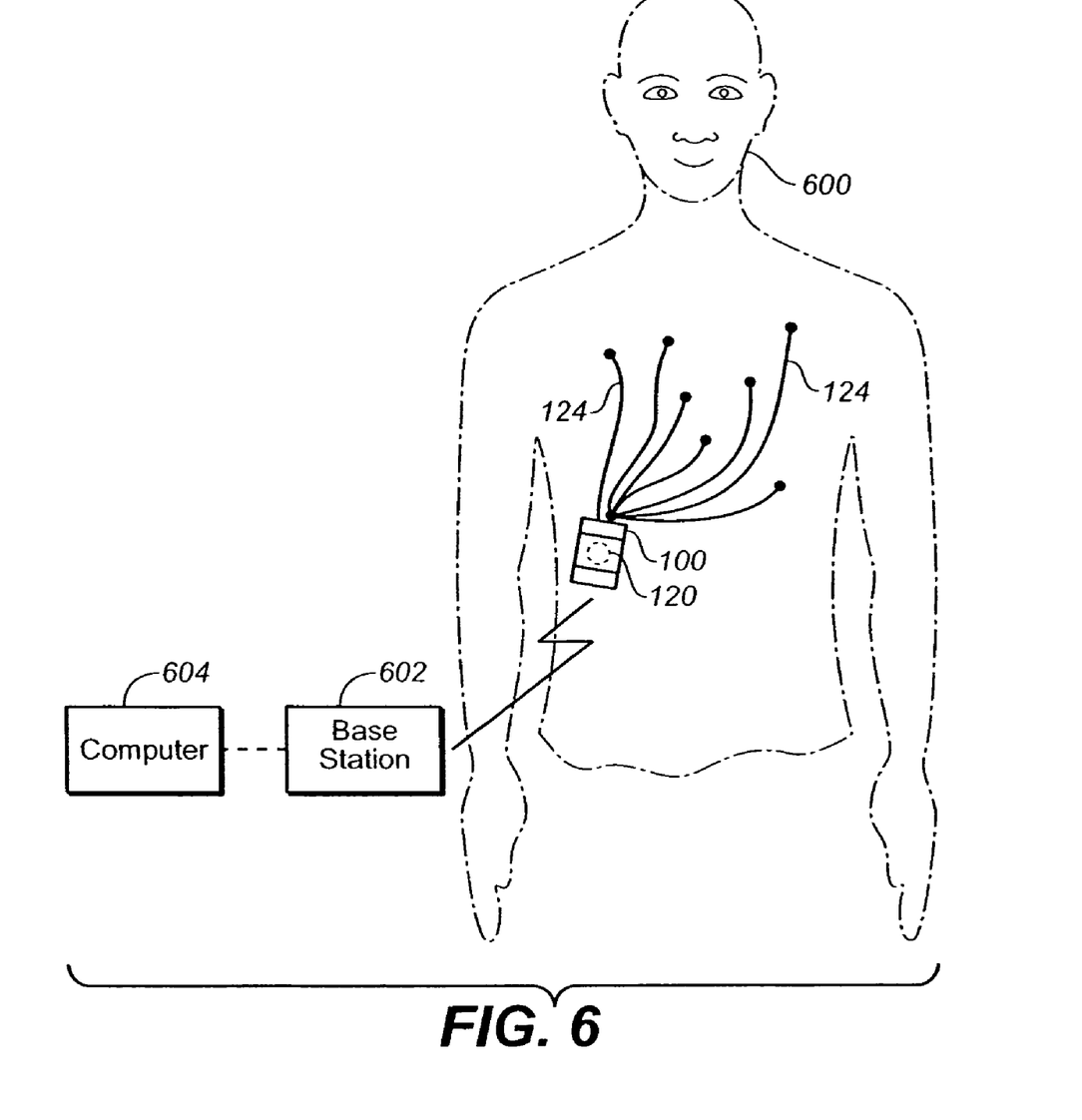
FIG. 6 is an illustration of the ECG monitor of FIG. 1 attached to a patient.

Referring to FIG. 6, the ECG monitor 100 attached to an ambulatory patient 600 is shown. The electrode leads 124 are placed at various locations on the patient's 600 chest region. The ECG monitor 100 is also adhered to the patient 600. For example, a second piece of tape that has a double sided adhesive is placed on the backside of the ECG monitor 100. The side of the ECG monitor 100 with the annotate button 120 would be accessible by the patient. Alternatively, the ECG monitor 100 may be transported on a band around the patient's arm, clipped to the patient's clothing, or attached to the patient 600 with surgical tape.

A base station 602 may be held close to the ECG monitor 100 for RF communication as the patient monitoring is in progress. To view the three sets of ECG waveforms, the base station 602 can be connected to a computer 604, via a cable such as a USB cable. The computer 604 includes software to process (if necessary) and display the sample data obtained from the electrode leads 124.

The RF communication between the recorder module 104 and the base station 602 is configured to be a short-range link and also very low in power consumption. The transmission range of the loop antenna 420 is within a couple of inches and no more than about 12 inches. The RF link can be configured to not interfere with other possible RF signals nor FCC mandates. The RF link is further configured to not interfere with other device(s) inside or around the patient, such as a pacemaker. The RF link operates at a non-sensitive frequency, short transmission range, low transmission power, and/or a different RF modulation scheme to prevent interference issues.

The RF link implemented in the ECG monitor 100 operates at around 20 microamp of current. Alternatively, LEDs or an infrared communication link may be implemented instead of the RF link, operable around several milliamp of current.

Figure 7:
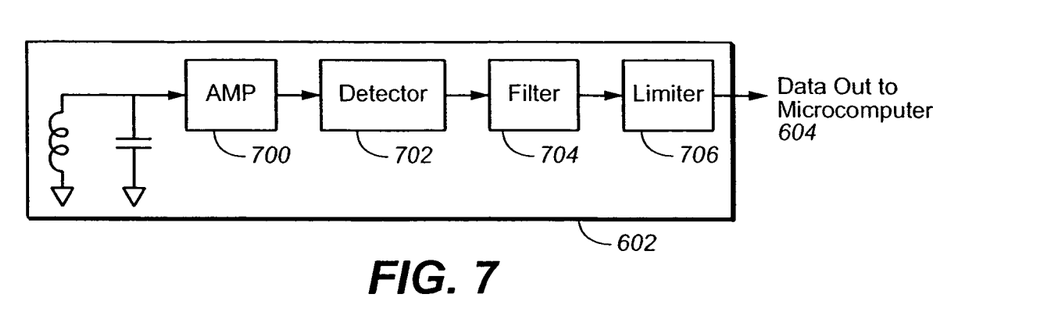
FIG. 7 is a block diagram of circuitry included in a base station.

FIG. 7 illustrates RF circuitry included in the base station 602. Although not shown, the RF circuitry includes a receiving RF antenna. After the RF antenna receives the RF signal, the RF signal is processed suitable for outputting to the computer 604. An amplifier 700 amplifies the RF signal. The amplified signal is inputted to a detector 702. When the amplified signal is determined to be a plausible RF signal transmitted by the recorder module 104, then the signal is inputted to a filter 704 and a limiter 788. The output of the limiter 706 is the input to the computer 604.

The ECG monitor 100 performs modulation of the ECG signals suitable for storage at the FIFO memory 416 and transmission via the loop antenna 420. In one embodiment, a data serializer circuitry may be included between the RF modulator 418 and the decimator 414.

In one embodiment, the ECG monitor 100 implements RF modulation using a FM coding scheme. FM coding scheme comprises modulation or coding based on transitions between a signal high and low (or vice versa), as opposed to the high or low values of the signal itself.

One bit of modulated output is generated from two successive presubscribed minimum time periods of signal information (e.g., each presubscribed minimum time period referred to as a "binit period"). No more than two binit periods occur without an occurrence of a transition. A transition is considered to be any change in state from an on to off, off to on, high to low, or low to high. For example, the instant that the RF communication link starts or turns off is considered a transition.

Figure 8A:
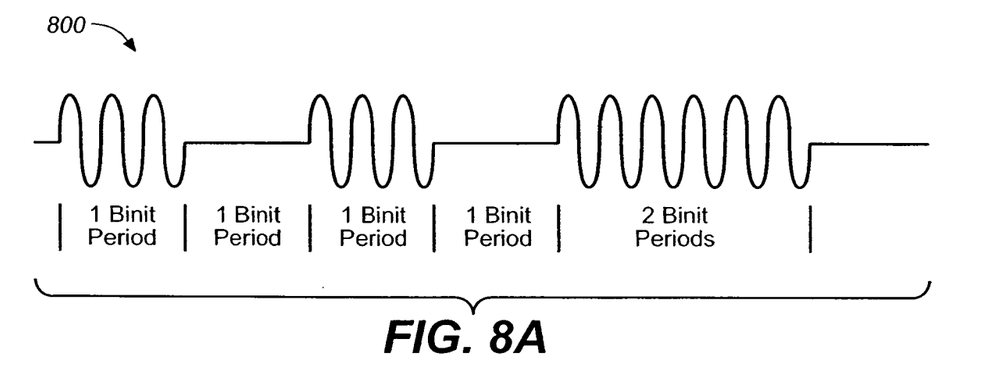
FIG. 8 illustrates ECG waveforms obtained by the ECG monitor of FIG. 1 at different stages of signal processing.
Figure 8B:
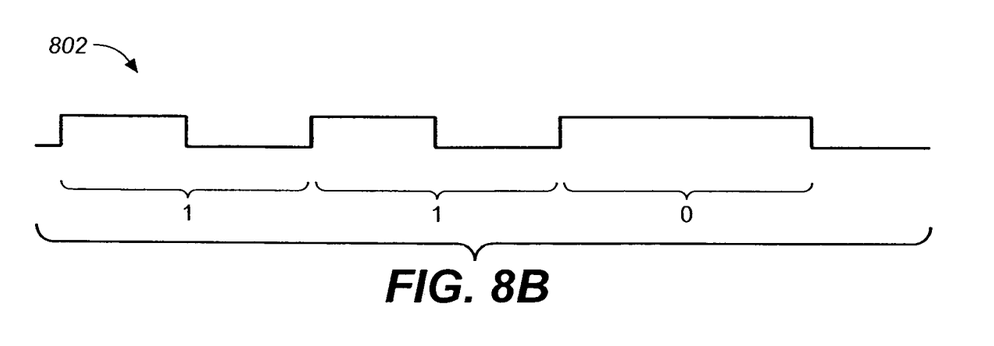

A data bit of "0" in the modulated output is representative of two successive binit periods of data, where the two binit periods can start and/or end with a transition but there is no transition between the two binit periods. A data bit of "1" in the modulated output is representative of two successive binit periods of data, where the two binit periods can start and/or end with a transition and there is a transition between the start and end points of the two binit periods. A signal or waveform 800 shown in FIG. 8(a) is representative of an input signal to undergo FM coding. A signal or waveform 802 shown in FIG. 8(b) is representative of the input signal 800 of FIG. 8(a) after processing by a limiter or half-wave rectifier, thereby converted to a digital or logic type of signal. Lastly, the signal 802 modulated with FM coding would be represented as three bits of data: 110.

Figure 8C:
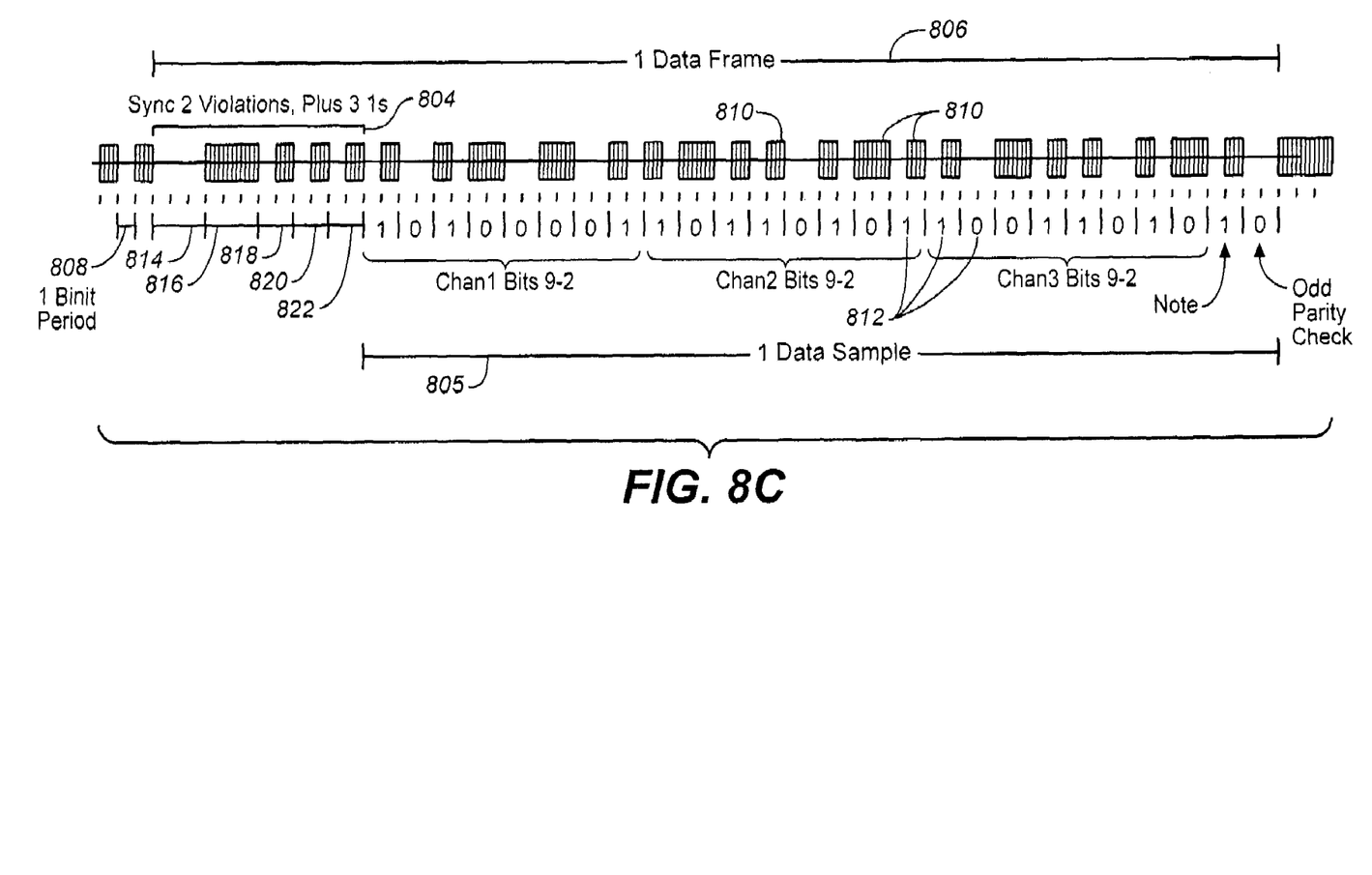

To designate the start of a different data sample, such as the sample 500, a synchronization event or information is included immediately before the start of each data sample. As shown in FIG. 8(c), a synchronization data portion 804 is provided immediately before a data sample 805. The combination of the synchronization data portion 804 and the data sample 805 is collectively referred to as a data frame 806. In FIG. 8(c), each unit of the data frame 806 is designated as a binit period 808. Waveform or signals 810 is representative of a limiter output signal (e.g., the signal 802), and bits 812 are representative of the signals 810 after application of the FM coding scheme.

The synchronization data portion 804 comprises at least a pair of timing or coding violations. Recall with the FM coding scheme, that there would be no more than 2 successive binit periods without a transition. However, in the synchronization data portion 804, there are 3 successive binit periods without a transition and this happens twice in a row (first sync pattern 814 and second sync pattern 816). In addition, the first and second sync patterns 814 and 816 are followed by 3 sets of 2 binit periods each having a transition (third, fourth, and fifth sync patterns 818, 820, 822). The third, fourth, and fifth sync patterns 818, 820, 822 are collectively referred to as a preset coded sequence. Thus, the synchronization data portion 804 is comprised of 2 "violations" followed by 3 "1"s, expressed as bits 010111 after FM coding scheme application.

In an alternate embodiment, the synchronization data portion 804 comprises other data patterns recognizable as data sample separators. For example, the synchronization data portion 804 can comprise more or less than one coding violation. As another example, the synchronization data portion 804 need not include a preset coded sequence such as the third, fourth, and fifth sync patterns 818, 820, 822.

The data sample 805 comprises data samples obtained from the ambulatory patient and outputted by the decimator 414. For example, the data sample 805 can be the data sample 500.

In this manner, analog ECG signals obtained from the patient are encoded for accurate data transfer via a RF communication link. The modulated data further includes annotation information (indicative of the state of the annotate switch 417) and error check information to facilitate use of the ECG signal data at the base station 602 and/or computer 604. At the end of each sample period, a data sample is outputted from the decimator 414 and is transmitted to each of the FIFO memory 416 and the RF modulator 418. The RF modulator 418 is configured to apply the FM coding to the received data sample and to drive the RF transmission via the loop antenna 420.

In an alternate embodiment, a modulation scheme other than FM coding can be implemented in the ECG monitor 100. As an example, a modified FM (MFM) coding scheme or any coding scheme that is compatible with RF transmission may be utilized.

Figure 9:
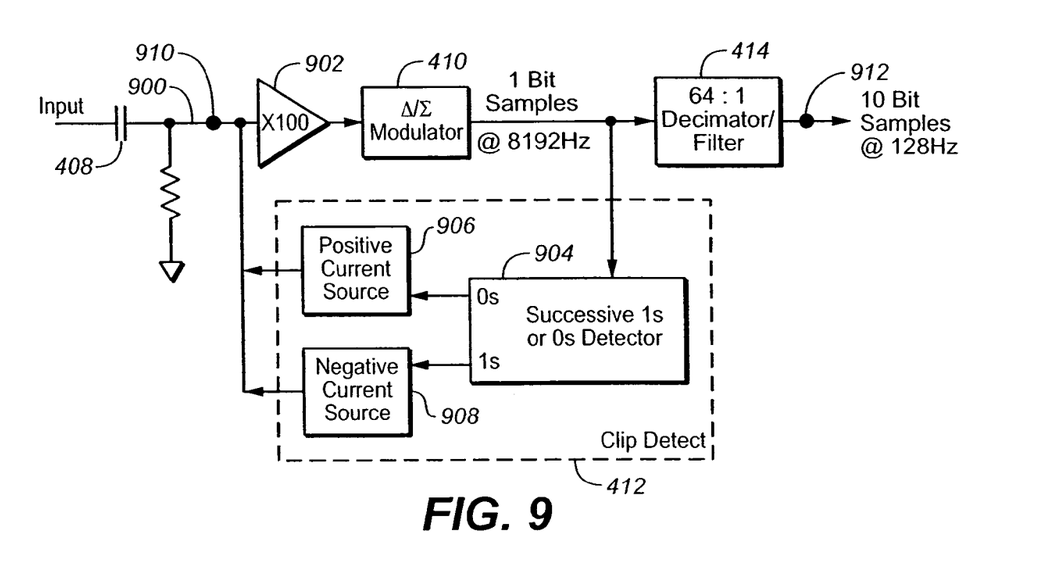
FIG. 9 is a more detailed block diagram of circuitry included in the ECG monitor of FIG. 1 associated with a signal clipping feature.

Referring to FIG. 9, a detailed block diagram of a portion of the converter IC chip 116 is shown. The circuit blocks associated with detection and correction of out-of-range signals for each channel are shown. This range limiter or clip correction occurs independently at each of the three channels of the ECG monitor 100. During initialization or calibration of the ECG monitor 100, the health care professional specifies whether or not to engage the clip correction feature. Selection of clip correction is specified via RXD and TXD lines to the microcontroller IC chip 114. The microcontroller IC chip 114 includes a certain amount of flash memory to permit programming and retention of certain settings, such as the clip correction feature selection.

Although the clip correction feature is optional, healthcare personnel reviewing or analyzing the obtained data (e.g., cardiologists) may find the feature to be valuable. Without the clip correction feature, ECG signals can go off-scale for several seconds at a time so that no useable waveform data is recorded for such periods of time. ECG signals can go off-scale (also referred to as being out-of-range) when the baseline or "zero" point of the signal range significantly changes during the recording period. Such significant, and often abrupt, changes to the baseline occurs from events such as: change in electrical potential between different electrodes, change in patient's skin chemistry (e.g., perspiration), some kind of change to the electrodes itself, the patient shifting body position, patient under stress from some cardiac event, etc. Ambulatory ECG monitors in compliance with the EC38 standard are required to tolerate an input offset between 2 to 300 millivolts. Nevertheless, a normal heartbeat signal is typically on the order of only 1 millivolts. Thus, continuously tracking an input signal on the order of 1 millivolts in the context of events occurring during the recording period responsible for significant baseline fluctuations and large input signal amplification schemes results in certain ECG signals being out of range for certain periods of time. In contrast, with the clip correction feature activated, an out-of-range ECG signal is brought within range in less than one data sample period.

In FIG. 9, analog signals 900 (the output of the coupling capacitor 408) are the input to the nth order delta-sigma modulator 410. The analog signals 900 are amplified by an amplifier 902 prior to processing at the nth order delta-sigma modulator 410. The output of the nth order delta-sigma modulator 410 is the input to the clip detector 412. The clip detector 412 forms a feedback loop to the input line. The output of the nth order delta-sigma modulator 410 is also the input to the decimator 414.

The nth order delta-sigma modulator (or converter) 410 is configured to output clocked signal bits based on the analog input signals 900. The nth order delta-sigma modulator 410 provides an output bit rate that is higher than the intended output sample rate. In one embodiment, the nth order delta-sigma modulator outputs at 64 times the intended output sample rate. Hence, continuing the earlier example of operating the ECG monitor 100 at a 128 Hz sampling rate, the output of the nth order delta-sigma modulator are 1 bit samples at 8192 Hz (see FIG. 9). In an alternate embodiment, the nth order delta-sigma modulator 410 may comprise an over-sampling converter.

The decimator 414 is configured to bring the one bit samples at the high sample rate (from the nth order delta-sigma modulator 410) to multi-bit samples at a lower sample rate. A decimation ratio associated with the decimator 414 can range between 16:1 to 256:1. Continuing the 128 Hz sampling rate example, the decimator 414 has a 64:1 input to output sample rate ratio. The output of the decimator 414 is 10 bit samples at 128 Hz (see FIG. 9). The decimator 414 (which includes at least one filter) is configured to expand the obtained data to improve accuracy. Accuracy is improved by effectively averaging a large number of single bit input signals or bits (in other words, averaging over a number of data samples).

However, there is a delay of many data samples associated with the averaging function in the decimator 414. Thus, if the output of the decimator 414 was utilized to determine if the obtained ECG signal was out-of-range, then the actual out-of-range condition could not be known until many data samples after the actual point in time when it occurred.

Instead, FIG. 9 illustrates the out-of-range signal detection using the clip detector 412. The detector 412 includes a detector 904, a positive current source 906, and a negative current source 908. The output of the nth order delta-sigma modulator 410 is provided to each of the detector 904 and the decimator 414. The output of the detector 904 is provided to each of the positive and negative current sources 906, 908. The output of each of the positive and negative current sources 906, 908 are combined and fed back to the input line (forms a feedback loop). The input of the nth order delta-sigma modulator 410 are the analog electrical potential signals sensed from the patient's body surface. The outer surface of the patent's skin around the chest region (non-invasively) provides signals representative of the electrical potential associated with the patient's heart muscle activity. The output of the decimator 414 is a digital ECG signal suitable for storage and/or RF transmission.

The detector 904 is configured to detect a prescribed number of successive 1's or 0's in the modulator 410 output bit stream. Detection of the prescribed number of successive 1's indicates that the obtained ECG signal is about to (or has started to) reach the positive maximum of the recordable magnitude range. A series of successive 1's may occur when the baseline of the obtained ECG signal shifts significantly in the positive direction (e.g., due to perspiration, patient movement, shift in contact point between electrode and patient, etc.) such that the positive peak value of the ECG signal exceeds the capturable range of the monitor 100. Alternatively, a series of successive 1's may occur when the patient is experiencing an extreme cardiac event such that the positive peak value of the ECG signal exceeds the capturable range of the monitor 100. Instead, the positive peak value of the ECG signal is detected as a "continuous" maximum value, which is digitized as a series of successive 1's. It is unlikely that the true positive peak value of the ECG signal would be a constant value for such a long period of time. Thus, a "continuous" and constant peak value detected is indicative of a clipped, saturated or out-of-range condition.

Conversely, detection of the prescribed number of successive 0's indicates that the obtained ECG signal is near or at the negative maximum of the recordable magnitude range. A series of successive 0's may occur when the baseline of the obtained ECG signal shifts significantly in the negative direction or due to an extreme cardiac event (e.g., due to perspiration, patient movement, shift in contact point between electrode and patient, etc.) such that the negative peak value of the ECG signal cannot be captured by the monitor 100. Similar to the successive 1's discussed above, a "continuous" and constant negative peak value detected is indicative of a clipped, saturated or out-of-range condition.

In one embodiment, 32 successive 1's is the prescribed number of 1's to trigger an out-of-range condition. The 32 successive 1's indicate that the analog signal obtained from the patient is within approximately 6% of the positive maximum. Similarly, 32 successive 0's is the prescribed trigger for the negative maximum being within approximately 6%.

If the successive 1's are detected for a positive maximum out-of-range condition, then the negative current source 908 pulls the current in one direction to bring down the baseline of the incoming analog signals 900 entering the amplifier 902. The negative current source 908 provides a negative current of certain magnitude to cause subsequent analog signals 900 to be within recordable range within less than a data sample period. The negative current source 908 is also configured to provide different magnitudes of negative current depending on the amount of correction required to bring the subsequent signals within the modulator's 410 active range. In other words, the negative current source 908 provides qualitative and quantitative correction functionality.

If the successive 0's are detected, then correspondingly the positive current source 906 pulls the current in the other direction to bring the baseline up. Otherwise, the positive current source 906 functions similar to the negative current source 908.

The positive and negative currents sources 906, 908 are configured to generate a positive or negative current, respectively, sufficient to affect the charge of, and thus the voltage across, the corresponding external coupling capacitor 408 by approximately 1 to 40% of its maximum voltage range within the modulator's 410 clock period. The voltage at a node 910 (the external coupling capacitor 408 terminal connected to the input of the nth order delta-sigma modulator 410) has a voltage range proportional to the maximum voltage range at a node 912 (output of the decimator 414).

For example, the maximum voltage range at the node 912 may be +/−20 mV about a central bias voltage (40 mV total). The resistance at the node 910 can be 5 MΩ.

When at least a preset series of successive 1's or 0's is detected at the output of the nth order delta-sigma modulator 410, one of the positive or negative current sources 906, 908 (depending on the 1's or 0's detected) is actuated to affect the charge of the corresponding external coupling capacitor 408. This charging, in turn, results in a voltage change at the node 910. The rate of change of voltage at the node 910 is configured such that the new voltage at the node 910 is achieved within a single modulator 410 clock period. The new voltage is a voltage value brought closer to the central bias voltage or null voltage value (scaled down) by approximately 1 to 40% of the full scale (or maximum) voltage range. Continuing the above example of a maximum voltage range of 40 mV at a 128 KHz sampling rate, the voltage change would be between approximately 0.4 mV to 16 mV within a 1/8192 th of a second. For an external coupling capacitor having a capacitance of 1 μF, for example, the current required to affect a voltage change of 0.4 to 16 mV would be between 3.3 to 130 μA, respectively.

Since the modulator 410 outputs are as close as possible to real-time indicators of how extreme in magnitude the analog ECG signals are, continuously monitoring such outputs and introducing offsets to subsequent analog signals as soon as possible allow out-of-range ECG signals to be brought back into range within a very short time period (e.g., within less than the time period of a heartbeat, less than the sampling period, within the A/D modulator clock period, or substantially in real-time).

The heartbeat waveforms during the vast majority of the out-of-range time period is thus accurately recorded (as is done for in-range waveforms), which is useful for diagnostic purposes, even though there is amplitude scale distortion from "forcing" the signals within a useable range. The abrupt shift in the baseline would indicate to the person viewing the recorded data that the clip correction had been implemented.

In another embodiment, it is contemplated that more or less than 32 successive 1's or 0's needs to be detected to trigger the clip detector feature. The trigger of the detector 904 can be preset to between 5 to 128 successive 1's or 0's. The minimum number of successive 1's or 0's required may depend, for example, on how close the input analog signal should be to a maximum (e.g., more or less than 6% of maximum) or how fast clip correction is to be initiated.

Thus the ECG monitor 100 takes analog electrical potential signals associated with a person's cardiac activity, and processes these signals suitable for storage and/or RF transmission. These signals are A/D converted using nth order delta-sigma modulators 410 and the decimator 414. The addition of the clip detectors 412 and associated circuitry during A/D conversion permit early detection of overflow conditions then would otherwise be possible. The resulting digital output signals at the decimator 414 are highly accurate, lower rate signals than the data bitstream from the nth order delta-sigma modulators 410.

Figure 10:
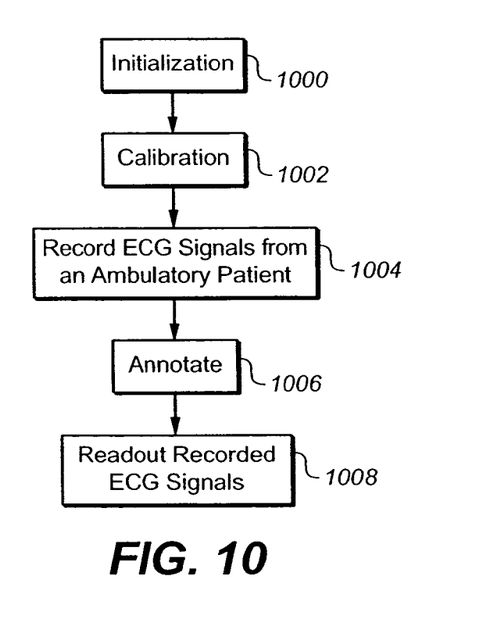
FIG. 10 is a flow diagram illustrating the utilization of the ECG monitor of FIG. 1.

Referring to FIG. 10, a flow diagram illustrates the use of the ECG monitor 100. At a block 1000, the health care professional (e.g., physician, nurse, physician assistant, etc.) initializes the ECG monitor 100 for a new patient. The health care professional inserts new batteries into the recorder module 104; and slides the first and second covers 102, 106 over the recorder module 104. Next, the annotate button 120 is depressed as the batteries are inserted and for some minimum period of time (e.g: 5 seconds or 10 seconds) after battery insertion. This causes the microcontroller IC chip 114 to power up and erase the FIFO memory 416 and the flash memory IP chip 400. In other words, the ECG monitor 100 is reset to record data for a new patient. Since the recorder module 104 is reusable, the recorder module 104 may contain data recorded from a previous patient, which should be erased for the new patient via the initialization process.

At the block 1000, the recorder module 104 or the ECG monitor 100 may be connected to the computer 604 via the pin connector 118. The flash memory IC chip 400 can then be provided with patient identifying information such as the patient's name, date, case number, brief patient history, etc. Alternatively, patient identifying information need not be included since such information can be provided on a label or bag with the completely recorded recorder module 104.

If the electrode leads 124 are of the disposable variety, then a new set is connected to the ECG monitor 100. Lastly, a new moisture resistant device 300 (also referred to as the tape) is wrapped around the ECG monitor 100.

At the block 1002, the other end of the electrode leads 124 are attached to the patient's skin at the chest region. The ECG monitor 100 is also attached to the patient (e.g., patient's chest region) or the patient's clothing.

The health care professional holds the base station 602 close to the ECG monitor 100 to specify a desired sampling rate, to check that the batteries are functional, and/or to adjust the electrode leads 124 positions on the patient, each via the RF interface or the pin connector 118. It should be understood that these features can also be accomplished by coupling the ECG monitor 100 to the computer 604 (using a cable).

The desired sampling rate is provided to the microcontroller IC chip 114. The health care professional can select from 128 Hz, 256 Hz, 522 Hz, or 1024 Hz sampling rates. The sampling rate would depend, for example, on the degree of sensitivity of ECG data desired, the length of recording time, memory capacity, and/or battery capacity.

Although initiation and calibration are illustrated as separate blocks 1000 and 1002, respectively, one or more of the steps can be performed simultaneously, in different order, or omitted than as discussed above. As an example, the ECG monitor 100 may provide a default sample (or sampling) rate of 128 Hz.

Once initialization and calibration are complete, recording of a patient's ECG signals starts at a block 1004. The patient is typically free to go about his/her regular routine in an outpatient environment. Such regular routine can include showering, exercising, and sleeping with the attached ECG monitor 100.

During the recording period, if the patient notices an irregular physical symptom or event, he can annotate the corresponding ECG signals being recorded at that same moment in time (block 1006). The patient presses the annotate button 120 which is accessible through the tape. The patient can annotate more than once and at any time during the recording period. Such annotation (or flag) highlights time periods worthy of closer attention or study.

During the recording period, if the flash memory IC chip 400 becomes full, then the microcontroller IC chip 114 turns off the recorder module 104 (including the converter IC chip 116, flash memory IC chip 400, and the microcontroller IC chip 114). This ensures that needless battery usage that could lead to battery leakage and/or damage to the ECG monitor 100 does not occur.

Lastly, at a block 1008, the patient returns to the health care professional to return the recorded ECG monitor 100.

Typically, the patient is instructed to allow the recording to occur for a set period of time (e.g., 24 hours, 48 hours, 72 hours, etc.). The ECG data stored in the flash memory IC chip 400 is retrieved via the pin connector 118 to the base station 602 or the computer 604. Depending on the power source at the base station 602 or the computer 604, no power source is required at the ECG monitor 100 for data readout. For example, if the ECG monitor 100 is accessed via a USB cable, the USB cable can also provide power to the ECG monitor 100.

When the recorded data is displayed (at the computer 604 or printed on paper), three sets of ECG traces corresponding to the three differential channels are provided. These traces also include the annotate condition information. Depending on the software at the computer 604, the displayed traces can be representative of further processed data.

In this manner, a system and method for recording ECG signals for an extended period of time are disclosed herein. ECG signals from an ambulatory patient can be obtained away from a health care professional or hospital setting. The ECG monitor is inexpensive, lightweight, small, and robust. Certain parts of the ECG monitor are disposable, to facilitate hygiene criteria and maximum performance. Although the ECG monitor is diminutive, a wide range of features are provided. Among other, various sampling rates, optimization of ECG signal obtaining locations on the patient, rapid detection and correction of out-of range signals, and real-time data output are provided.

While the invention has been described in terms of particular embodiments and illustrated figures, those of ordinary skill in the art will recognize that the invention is not limited to the embodiments or figures described. For example, the recorder module 104 can be encased by a one piece cover having a water resistant lid, rather than the first and second covers 102, 106 and the moisture resistant device 300. As another example, the functionalities of the IC chips 116, 114, 400 may be provided on a single IC chip to facilitate further reduction in the size of the ECG monitor. As still another example, the flash memory IC chip 400 may be upgradeable in the recorder module 104 as higher capacity, higher data transfer speed, and/or lower power consuming flash memory chips become available.

One or more aspects of one or more embodiments may be combined to form additional embodiments. The figures provided are merely representational and may not be drawn to scale. Certain proportions thereof may be exaggerated, while other may be minimized. The figures are intended to illustrate various implementations of the invention that can be understood and appropriately carried out by those of ordinary skill in the art. Therefore, it should be understood that the invention can be practiced with modification and alteration within the spirit and scope of the appended claims. The description is not intended to be exhaustive or to limit the invention to the precise form disclosed. It should be understood that the invention can be practiced with modification and alteration. From the foregoing, it will be appreciated that specific embodiments of the invention have been described herein for purposes of illustration, but that various modifications may be made without deviating from the spirit and scope of the invention. Accordingly, the invention is not limited except as by the appended claims and equivalents thereof.

What is claimed is:

1. Circuitry for obtaining electrocardiogram (ECG) signals associated with an ambulatory patient, the circuitry comprising:

a first integrated circuit (IC) configured to accept differential channels of ECG signals, process the ECG signals, and store the processed ECG signals, wherein capacitors are coupled to the first IC to correct out-of-range ECG signals;

a second IC in communication with the first IC, the second IC including a microcontroller; and a third IC in communication with the second IC, the third IC configured to store the processed ECG signals from the first IC, wherein each of the second and third ICs is selectively powered in response to an approximately full capacity of the stored processed ECG signals in the first IC.

2. The circuitry of claim 1, wherein the first, second, and third ICs are provided in a recorder module weighing less than approximately 16 grams.

3. The circuitry of claim 1, further comprising:

an antenna coupled to the first IC, wherein the first IC includes a radio frequency (RF) modulator and the antenna transmits the processed ECG signals in real-time.

4. The circuitry of claim 1, wherein the stored processed ECG signals include data associated with each of the differential channels, a condition of a notation switch, and an error check.

5. The circuitry of claim 1, wherein the first IC includes a clip detector.

6. The circuitry of claim 1, wherein the second IC shuts off power to the first, second, and third ICs when the third IC has reached full storage capacity.

7. The circuitry of claim 1, further comprising:

a notation switch coupled to the first IC, wherein the stored processed ECG signals include data associated with a condition of the notation switch.

8. The circuitry of claim 1, wherein the first, second, and third ICs are provided in a recorder module having an average current consumption of less than 1 milliamp.

9. Circuitry for obtaining electrocardiogram (ECG) signals associated with an ambulatory patient, the circuitry comprising:

a first integrated circuit (IC) configured to accept differential channels of ECG signals, process the ECG signals, and store the processed ECG signals;

a second IC in communication with the first IC, the second IC including a microcontroller; and a third IC in communication with the second IC, the third IC configured to store the processed ECG signals from the first IC, wherein each of the second and third ICs is selectively powered in response to an approximately full capacity of the stored processed ECG signals in the first IC, an antenna is coupled to the first IC, the first IC includes a radio frequency (RF) modulator, and the antenna transmits the processed ECG signals in real-time.

10. The circuitry of claim 9, further comprising:

capacitors coupled to the first IC to correct out-of range ECG signals.

11. The circuitry of claim 9, wherein the antenna transmits within a range of less than approximately 12 inches.

12. The circuitry of claim 9, wherein the stored processed ECG signals include data associated with each of the differential channels, a condition of a notation switch, and an error check.

13. The circuitry of claim 9, wherein the first IC includes a clip detector.

14. The circuitry of claim 9, further comprising:
a notation switch coupled to the first IC, wherein the stored processed ECG signals include data associated with a condition of the notation switch.

15. The circuitry of claim 9, wherein the first, second, and third ICs are provided in a recorder module having an average current consumption of less than 1 milliamp.

16. Circuitry for obtaining electrocardiogram (ECG) signals associated with an ambulatory patient, the circuitry comprising:
a first integrated circuit (IC) configured to accept differential channels of ECG signals, process the ECG signals, and store the processed ECG signals, wherein the first IC includes a clip detector;
a second IC in communication with the first IC, the second IC including a microcontroller; and
a third IC in communication with the second IC, the third IC configured to store the processed ECG signals from the first IC,
wherein each of the second and third ICs is selectively powered in response to an approximately full capacity of the stored processed ECG signals in the first IC.

17. The circuitry of claim 16, further comprising:
a notation switch coupled to the first IC, wherein the stored processed ECG signals include data associated with a condition of the notation switch.

18. The circuitry of claim 16, wherein the first, second, and third ICs are provided in a recorder module weighing less than approximately 16 grams.

19. The circuitry of claim 16, wherein the stored processed ECG signals include data associated with each of the differential channels, a condition of a notation switch, and an error check.

20. The circuitry of claim 16, wherein the first, second, and third ICs are provided in a recorder module having an average current consumption of less than 1 milliamp.

21. The circuitry of claim 16, further comprising:
Capacitors coupled to the first IC to collect out-of-range ECG signals.

22. Circuitry for obtaining electrocardiogram (ECG) signals associated with an ambulatory patient, the circuitry comprising:
a first integrated circuit (IC) configured to accept differential channels of ECG signals, process the ECG signals, and store the processed ECG signals;
a second IC in communication with the first IC, the second IC including a microcontroller; and
a third IC in communication with the second IC, the third IC configured to store the processed ECG signals from the first IC,
wherein each of the second and third ICs is selectively powered in response to an approximately full capacity of the stored processed ECG signals in the first IC, and wherein the second IC shuts off power to the first, second, and third ICs when the third IC has reached full storage capacity.

23. The circuitry of claim 22, further comprising:
capacitors coupled to the first IC to correct out-of-range ECG signals.

24. The circuitry of claim 22, further comprising:
an antenna coupled to the first IC, wherein the first IC includes a radio frequency (RF) modulator and the antenna transmits the processed ECG signals in real-time.

25. The circuitry of claim 22, wherein the stored processed ECG signals include data associated with each of the differential channels, a condition of a notation switch, and an error check.

26. The circuitry of claim 22, wherein the first IC includes a clip detector.

27. The circuitry of claim 22, further comprising:
a notation switch coupled to the first IC, wherein the stored processed ECG signals include data associated with a condition of the notation switch.

28. The circuitry of claim 22, wherein the first, second, and third ICs are provided in a recorder module having an average current consumption of less than 1 milliamp.

* * * * *